United States Patent
Bieberich et al.

(10) Patent No.: US 11,389,440 B2
(45) Date of Patent: Jul. 19, 2022

(54) PIM KINASE INHIBITORS IN COMBINATION WITH AUTOPHAGY INHIBITORS FOR TREATMENT OF CANCERS

(71) Applicant: UNIVERSITY OF MARYLAND, BALTIMORE COUNTY, Baltimore, MD (US)

(72) Inventors: Charles J. Bieberich, Brookeville, MD (US); Xiang Li, Baltimore, MD (US)

(73) Assignee: UNIVERSITY OF MARYLAND, BALTIMORE COUNTY, Baltimore, MD (US)

( * ) Notice: Subject to any disclaimer, the term of this patent is extended or adjusted under 35 U.S.C. 154(b) by 82 days.

(21) Appl. No.: 16/753,006

(22) PCT Filed: Oct. 3, 2018

(86) PCT No.: PCT/US2018/054056
§ 371 (c)(1),
(2) Date: Apr. 2, 2020

(87) PCT Pub. No.: WO2019/070777
PCT Pub. Date: Apr. 11, 2019

(65) Prior Publication Data
US 2020/0230125 A1 Jul. 23, 2020

Related U.S. Application Data

(60) Provisional application No. 62/567,829, filed on Oct. 4, 2017.

(51) Int. Cl.
| | |
|---|---|
| *A61K 31/4706* | (2006.01) |
| *A61K 31/365* | (2006.01) |
| *A61K 31/409* | (2006.01) |
| *A61K 31/426* | (2006.01) |
| *A61K 31/454* | (2006.01) |
| *A61K 31/5025* | (2006.01) |
| *A61K 31/551* | (2006.01) |
| *A61P 35/00* | (2006.01) |
| *A61K 45/06* | (2006.01) |

(52) U.S. Cl.
CPC ........ *A61K 31/4706* (2013.01); *A61K 31/365* (2013.01); *A61K 31/409* (2013.01); *A61K 31/426* (2013.01); *A61K 31/454* (2013.01); *A61K 31/5025* (2013.01); *A61K 31/551* (2013.01); *A61K 45/06* (2013.01); *A61P 35/00* (2018.01)

(58) Field of Classification Search
CPC .............. A61K 31/4706; A61K 31/365; A61K 31/409; A61K 31/426; A61K 31/454; A61K 31/5025; A61K 31/551
See application file for complete search history.

(56) References Cited

U.S. PATENT DOCUMENTS

2016/0038495 A1    2/2016   Kuo et al.

FOREIGN PATENT DOCUMENTS

WO    WO 2017-165495 A1    9/2017

OTHER PUBLICATIONS

Chen et al., Inhibition of Autophagy Enhances SMI-4a-induced Growth Inhibition and Apoptosis of Melanoma Cells, Tropical Journal of Pharmaceutical Reasearch, vol. 17, No. 3, pp. 401-407. (Year: 2018).*
Frankel, L. B., Lubas, M., and Lund, A. H. (2017) Emerging connections between RNA and autophagy. Autophagy 13, 3-23.
Levy, J. M. M., Towers, C. G., and Thorburn, A. (2017) Targeting autophagy in cancer. Nat Rev Cancer 17, 528-542.
Chou, T. C., and Talalay, P. (1984) Quantitative analysis of dose-effect relationships: the combined effects of multiple drugs or enzyme inhibitors. Adv Enzyme Regul 22, 27-55.
Cervantes-Gomez, F. et al., Clinical Lymphoma, Myeloma & Leukemia, 2013, vol. 13, Suppl. 2, pp. S3 1 7-S329.
Mans, L. A. et al., Scientific Reports, Aug. 4, 2017, vol. 7, Article No. 7327, pp. 1-10.
Zhao, Y. Q. et al., Acta Pharmacologica Sinica, 2016, Vo. 37, No. 9, pp. 1237-1250.

* cited by examiner

*Primary Examiner* — Brenda L Coleman
(74) *Attorney, Agent, or Firm* — Marianne Fuierer; Casimir Jones, S.C.

(57) ABSTRACT

The present invention provides for a method of treating cancer and/or reducing proliferation of cancer cells, the method comprising administering to a subject in need of such treatment a composition comprising a PIM kinase inhibitor that exhibits changes in expressed RNA or ribosomal binding proteins in combination with a compound that inhibits autophagy.

7 Claims, No Drawings

PIM KINASE INHIBITORS IN COMBINATION WITH AUTOPHAGY INHIBITORS FOR TREATMENT OF CANCERS

CROSS-REFERENCE TO RELATED APPLICATIONS

This application is filed under the provisions of 35 U.S.C. § 371 and claims the priority of International Patent Application No. PCT/US2018/054056 filed on Oct. 3, 2018 which in turn claims priority to U.S. Provisional Patent Application No. 62/567,829 filed on Oct. 4, 2017, the contents of which is hereby incorporated by reference herein for all purposes.

BACKGROUND OF THE INVENTION

Field of the Invention

The present invention relates to the treatment of a cancer in a patient through administration of a PIM kinase inhibitor in combination with an autophagy inhibitor.

Related Art

In the treatment of human diseases, resistance to chemotherapeutic agents is a growing problem. The situation is particularly acute in the treatment of malignancies: rapid cell division rates combined with genomic instability provides fertile ground for the emergence of, and positive selection for, mutations that confer drug resistance. One potential solution to this intransigent problem is to combine therapeutic agents to achieve tumor control. For example, combinations of targeted agents, or combinations of targeted agents and conventional chemotherapies can be envisaged. The difficulty in taking this approach lies in determining which combinations of two or more agents will be effective.

Kinases are enzymes that are major drivers of oncogenic processes in the cell. Virtually all cancer cases involve over-activation of one or more kinases. Kinase inhibition has emerged as a major therapeutic entry point for cancer treatment. The paradigm for this approach is the small molecule BCR-ABL kinase inhibitor Gleevec. While Gleevec has met with phenomenal clinical and commercial success, few other kinase inhibitors are clinically available, due, in large measure, to their lack of efficacy in vivo at their clinically applicable doses. One potential solution to this problem is to combine kinase inhibition with either another targeted drug, or a conventional chemotherapeutic agent. Currently, there is little information available to rationally guide the choice of agents to combine with kinase inhibitors. This lack of information stems from the fact that, for most kinases, there is a limited view of the downstream pathways that they regulate.

Pro-growth kinase up-regulation is a common feature of nearly all cancers and a major target for therapeutic intervention. Proviral integration site for Moloney murine leukemia virus (PIM) kinases comprise a family of oncogenic kinases, which are deregulated in hematopoietic cancers including Acute Myeloid Leukemia (AML) as well as epithelial malignancies like prostate cancer. Several features of PIM kinases make them an excellent target for cancer therapy. PIM kinases are constitutively active and are dispensable for growth of most normal adult tissues. However, to date, very few substrates have been identified for PIM kinases.

Thus, it would be advantageous to fully characterize the physiological roles of PIM kinases and with such discovery provide a new combination of effective therapies to treat cancer.

SUMMARY OF THE INVENTION

The present invention relates to the discovery that PIM kinases interacts with RNA binding and/or ribosomal proteins that are known to regulate autophagy. As such, a PIM kinase inhibitor can be combined with an autophagy modulator/inhibitor to provide a synergistic combination that has the ability to inhibit proliferation of cancer cells.

In one aspect, the present invention provides for a method of treating cancer and/or reducing proliferation of cancer cells, the method comprising administering to a subject in need of such treatment a composition comprising a PIM kinase inhibitor that exhibits changes of RNA binding and/or ribosomal proteins that regulate autophagy in combination with a compound that inhibits autophagy.

The PIM kinase inhibitor may include, but is not limited to SGI-1776 (N-[(1-methylpiperidin-4-yl)methyl]-3-[3-(trifluoromethoxy)phenyl]imidazo[1,2-b]pyridazin-6-amine), SMI-4a (5-[[3-(trifluoromethyl)phenyl]methylidene]-1,3-thiazolidine-2,4-dione), CX-6258 (E)-5-chloro-3-((5-(3-(4-methyl-1,4-diazepane-1-carbonyl)phenyl)furan-2-yl)methylene)indolin-2-one), LKB1 (N-[5-(4-cyanophenyl)-1H-pyrrolo[2,3-b]pyridin-3-yl]pyridine-3-carboxamide), AZD1208 ((5E)-5-[[2-[(3R)-3-aminopiperidin-1-yl]-3-phenylphenyl]methylidene]-1,3-thiazolidine-2,4-dione), PIM-1 Inhibitor 2 (4-[3-(4-chlorophenyl)-2,1-benzoxazol-5-yl]pyrimidin-2-amine), R8-T198 wt and TCS PIM-1 (6-(5-bromo-2-hydroxyphenyl)-2-oxo-4-phenyl-1,2-dihydropyridine-3-carbonitrile).

An RNA or ribosomal protein that shows alteration is expression may be affected by a kinase inhibitor and such alterations have been found in genes encoding for RNA or ribosomal binding proteins. According to the present invention, such alterations are due to aberrant alternative splicing.

Splicing is a sequential process facilitated by the interaction of cis-sequence elements and trans-acting RNA-binding proteins (RBPs). Splicing can be highly variable as mRNA-RBP interactions are transient and of relatively low specificity. Changes in cis-sequence and levels of trans-factors can alter splicing and cause disease. Aberrant alternative splicing in genes effected by PIM kinase inhibitors include but not limited to:

SRSF1_HUMAN Serine/arginine-rich splicing factor 1 OS=*Homo sapiens* GN=SRSF1 PE=1 SV=2;
SRSF5_HUMAN Serine/arginine-rich splicing factor 5 OS=*Homo sapiens* GN=SRSF5 PE=1 SV=1;
SRSF6_HUMAN Serine/arginine-rich splicing factor 6 OS=*Homo sapiens* GN=SRSF6 PE=1 SV=2;
SRSF7_HUMAN Serine/arginine-rich splicing factor 7 OS=*Homo sapiens* GN=SRSF7 PE=1 SV=1;
SRS1O_HUMAN Serine/arginine-rich splicing factor 10 OS=*Homo sapiens* GN=SRSF10 PE=1 SV=1;
U2AF1_HUMAN Splicing factor U2AF 35 kDa subunit OS=*Homo sapiens* GN=U2AF1 PE=1 SV=3;
CWC22_HUMAN Pre-mRNA-splicing factor CWC22 homolog OS=*Homo sapiens* GN=CWC22 PE=1 SV=3;
SF3B2_HUMAN Splicing factor 3B subunit 2 OS=*Homo sapiens* GN=SF3B2 PE=1 SV=2;
SF01 HUMAN Splicing factor 1 OS=*Homo sapiens* GN=SF1 PE=1 SV=4;
SFR19 HUMAN Splicing factor, arginine/serine-rich 19 OS=*Homo sapiens* GN=SCAF1 PE=1 SV=3;

PR38A_HUMAN Pre-mRNA-splicing factor 38A OS=*Homo sapiens* GN=PRPF38A PE=1 SV=1;

SPF45 HUMAN Splicing factor 45 OS=*Homo sapiens* GN=RBM17 PE=1 SV=1;

SF3A2 HUMAN Splicing factor 3A subunit 2 OS=*Homo sapiens* GN=SF3A2 PE=1 SV=2;

HNRL2 HUMAN Heterogeneous nuclear ribonucleoprotein U-like protein 2OS=*Homo sapiens* GN=HNRNPUL2 PE=1 SV=1;

HNRPC HUMAN Heterogeneous nuclear ribonucleoproteins C1/C2 OS=*Homo sapiens* GN=HNRNPC PE=1 SV=4;

ROA1 HUMAN Heterogeneous nuclear ribonucleoprotein A1 OS=*Homo sapiens* GN=HNRNPA1 PE=1 SV=5;

ROA2 HUMAN Heterogeneous nuclear ribonucleoproteins A2/B1 OS=*Homo sapiens* GN=HNRNPA2B1 PE=1 SV=2;

RA1L2_HUMAN Heterogeneous nuclear ribonucleoprotein A1-like 2 OS=*Homo sapiens* GN=HNRNPA1L2 PE=2 SV=2;

ROA3 HUMAN Heterogeneous nuclear ribonucleoprotein A3 OS=*Homo sapiens* GN=HNRNPA3 PE=1 SV=2;

HNRPM HUMAN Heterogeneous nuclear ribonucleoprotein M OS=*Homo sapiens* GN=HNRNPM PE=1 SV=3;

HNRDL_HUMAN Heterogeneous nuclear ribonucleoprotein D-like OS=*Homo sapiens* GN=HNRNPDL PE=1 SV=3;

ROAO_HUMAN Heterogeneous nuclear ribonucleoprotein A/B OS=*Homo sapiens* GN=HNRNPAB PE=1 SV=2;

ROAA HUMAN Heterogeneous nuclear ribonucleoprotein A/B OS=*Homo sapiens* GN=HNRNPAB PE=1 SV=2;

HNRPK HUMAN Heterogeneous nuclear ribonucleoprotein K OS=*Homo sapiens* GN=HNRNPK PE=1 SV=1;

HNRPL HUMAN Heterogeneous nuclear ribonucleoprotein L OS=*Homo sapiens* GN=HNRNPL PE=1 SV=2;

ROA3_HUMAN Heterogeneous nuclear ribonucleoprotein A3 OS=*Homo sapiens* GN=HNRNPA3 PE=1 SV=2;

ROAO_HUMAN Heterogeneous nuclear ribonucleoprotein AO OS=*Homo sapiens*; GN=HNRNPAO PE=1 SV=1; and HNRPU HUMAN Heterogeneous nuclear ribonucleoprotein U OS=*Homo sapiens* GN=HNRNPU PE=1 SV=6.

Autophagy is a dynamic process involving the rearrangement of subcellular membranes to sequester cytoplasm and organelles for delivery to the lysosome or vacuole where the sequestered cargo is degraded and recycled. This process takes place in all eukaryotic cells. It is highly regulated through the action of various kinases, phosphatases, and guanosine triphosphatases (GTPases). A compound that inhibits autophagy may include antimalarial compounds such as chloroquine and hydroxychloroquine (HCQ), as well as the antidepressant agent clomipramine. Other compounds that have been found to inhibit autophagy include, but not limited to Bafilomycin A1, SBI-0206965, Spautin-1, SAR405, ATG4 inhibitors, such as NSC185058 and NSC377071, Verteporfin, ROC325, Lys05, NSC185058, 3-Methyladenine, Wortmanin, and LY294002.

In yet another aspect, the present invention provides for a composition comprising a PIM kinase inhibitor that exhibits changes and/or disruption of mRNA splicing of RNA or ribosomal proteins in combination with a compound that inhibits autophagy.

In a further aspect, the present invention provides for a synergistic combination of therapeutics for treating cancerous tissue and methods for the treatment of human cancers, including daily dosage forms for administration to cancer patients. The present invention provides for synergistic improvements in treatment outcomes by providing for a composition comprising therapeutically synergistic amounts of at least one a PIM kinase inhibitor that exhibits changes in RNA or ribosomal binding proteins in combination with a compound that modulates and/or inhibits autophagy, such that the combination has a therapeutic effect on cancerous tissue which is greater than the sum of the individual therapeutic effects of the individual compounds.

The PIM kinase inhibitors may include one or more kinases selected from the group consisting of: PIM-1, PIM-2, and PIM-3. Additional PIM kinase inhibitors, not previously mentioned above, may include but is not limited to 7-chloro-9-ethyl-6-hydroxyisoxazolo[3,4-b]quinoline-3,4 (1H,9H)-dione; 2-[[3-(3-chloro-4-fluorophenyl)imidazo[1,2-b]pyridazin-6-yl]amino]butan-1-ol; (Z)-5-(4-propoxybenzylidene)thiazolidine-2,4-dione; (Z)-5-(3-Trifluoromethylbenzylidene)thiazolidine-2,4-dione; N'-(1-(4-Chloro-2-hydroxyphenyl)propylidene)-2-((3-morpholinopropyl)amino-)isonicotinohydrazide; 5-amino-2-(2,6-difluorophenyl)-N-(5-(4-(methylamino)butoxy) isothiazol-4-yl)thiazole-4-carboxamide; 2-(2,6-difluorophenyl)-N-(5-(4-hydroxy-4-methylpentyloxy) isothiazol-4-yl)- -5-(methylamino)thiazole-4-carboxamide; (Z)-5-((2-(4-(((6-(furan-2-yl)pyridin-2-yl)methylamino) methyl)piperidin-1- -yl)pyrimidin-4-yl)methylene)thiazolidine-2,4-dione; (S)-5-amino-N-(4-(3-aminopiperidin-1-yl) pyridin-3-yl)-2-(2,6-difluorophenyl)thiazole-4-carboxamide; and N-(4-((3 S,5R)-3-amino-5-methylpiperidin-1-yl)pyridin-3-yl)-2-(2,6-difluorophenyl) thiazole-4-carboxamide, or a pharmaceutically acceptable salt thereof.

In yet another aspect, the PIM kinase inhibitor is a dual PIM-1/PIM-2 inhibitor. In various cases, the PIM kinase inhibitor is a pan-PIM inhibitor (e.g., inhibitors the activity of each of PIM-1, PIM-2, and PIM-3). One example of a contemplated pan-PIM inhibitor is 5-[[2-[(3R)-3-aminopiperidin-1-yl]biphenyl-3-yl]methylidene]-1,3-thiazolidine-2, 4-dione (also known as AZD1208).

The cancer to be treated with the proposed combination is one selected from the group consisting of: bone cancer, gynecological cancer, breast cancer, hematological malignancy, skin cancer, liver cancer, kidney cancer, pancreatic cancer, brain cancer, lung cancer, and prostate cancer. The hematological malignancy may be selected from the group consisting of: acute lymphoblastic leukemia (ALL), acute myeloid leukemia (AML), chronic lymphocytic leukemia (CLL), chronic myelogenous leukemia (CML), hairy cell leukemia, AIDS-related lymphoma, B-cell lymphoma, cutaneous T-cell lymphoma, Hodgkin lymphoma, non-Hodgkin lymphoma, mycosis fungoides, primary central nervous system lymphoma, Sezary syndrome, Waldenstrom macroglobulinemia, chronic myeloproliferative disorders, Langerhans cell histiocytosis, multiple myeloma, plasma cell neoplasms, myelodysplastic syndromes, myelodysplastic neoplasms, and myeloproliferative neoplasms.

In one aspect, the hematological malignancy is selected from the group consisting of: B-cell lymphoma and multiple myeloma. For example, the hematological malignancy can be multiple myeloma.

The administration of the PIM kinase inhibitor and a compound that inhibits autophagy is performed concurrently. Alternatively, the administration of the PIM kinase inhibitor and the compound that inhibits autophagy is performed sequentially, wherein the PIM kinase inhibitor is administered before the compound that inhibits autophagy or vice versa.

Aspects of the invention described as methods of treatment should also be understood to include first or subsequent "medical use" aspects of the invention or "Swiss use" of compositions for the manufacture of a medicament for treatment of the cancer.

In another aspect, the present invention provides for a combination of a PIM kinase inhibitor and a compound that inhibits autophagy for the use to treat cancers, wherein the PIM kinase inhibitor and a compound that inhibits autophagy are in a synergistic amount and ranging within a ratio of 1:800 to 1:1.

Multiple embodiments are contemplated for combination inventions described herein. For example, some aspects of the invention that are described as a method of treatment (or medical use) combining two or more compounds or agents, preferably in a synergistic amount, whether administered separately (sequentially or simultaneously) or in combination (co-formulated or mixed). For each aspect described in this manner, the invention further includes a composition comprising the two or more compounds or agents co-formulated or in admixture with each other; and the invention further includes a kit or unit dose containing the two or more compounds/agents packaged together. Optionally, such compositions, kits or doses further include one or more carriers with one or both agents or co-packaged for formulation prior to administration to a subject. The reverse also is true: some aspects of the invention are described herein as compositions useful for therapy and containing two or more therapeutic agents. Equivalent methods and uses are specifically contemplated.

Other features and advantages of the disclosure will be apparent from the following detailed description.

DETAILED DESCRIPTION OF THE INVENTION

The present invention provides for the discovery that inhibition of PIM family kinases synergizes with inhibition of a cellular process termed autophagy to block the proliferation of cancer cells. This result is achieved by profiling PIM kinase substrates using a reverse in-gel kinase assay, and determining that a plethora of direct targets of PIM kinase phosphotransferase activity are RNA binding and/or ribosomal proteins. RNA binding proteins are known to regulate autophagy (1), and autophagy is known to play roles supporting cell survival in some cancers (2). Therefore, the combination of PIM kinase inhibitors and autophagy inhibitors can be used to block the proliferation of cancer cells.

Further, it has been found that PIM kinase inhibitors disrupt normal mRNA splicing thereby causing altered splice site and/or exon recognition preferences relative to their wild-type counterparts, and can therefore be combined with others agents. PIM kinase inhibitor as provided herein can be any compound that inhibits or modulates the action of a PIM kinase. For example, the compound can inhibit and or modulate one or more of the serine/threonine kinases encoded by a PIM gene or protooncogene. In some embodiments, the serine/threonine kinase is one of three isoforms: PIM-1, PIM-2, and PIM-3. In some aspect, the PIM kinase inhibitors is a pan-PIM inhibitor and inhibits each of PIM-1, PIM-2, and PIM-3. The PIM kinase inhibitor is selective for PIM-1, PIM-2 and/or PIM-3. Examples of PIM kinase inhibitors can be found in: WO 2009/064486 and WO 2012/145617. Further contemplated PIM kinase inhibitors include those found in US20140031360, WO2012/129338, WO2012/148775, WO2013/130660 and WO2014/022752, the disclosures of which are each incorporated by reference herein in their entirety.

As used herein, the term "inhibitor" is meant to describe a compound that blocks, reduces or modulates an activity of an enzyme or system of enzymes, receptors, or other pharmacological target. An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme. The term inhibitor is used more broadly herein than scientific literature so as to also encompass other classes of pharmacologically or therapeutically useful agents, such as agonists, antagonists, stimulants, co-factors, and the like.

A "therapeutically effective amount" of a compound with respect to the subject method of treatment, refers to an amount of the compound(s) in a preparation which, when administered as part of a desired dosage regimen (to a patient, e.g., a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting one or more symptoms, clinical signs, and underlying pathology of a condition in a manner to improve or stabilize a patient's condition.

As used herein, the term "a synergistic effect" is present when the activity of the active compounds in a combination exceeds the total of the action of the active compounds when applied individually.

Methods of Use

Combination drug therapy is the use of two or more pharmacologic agents administered either separately or in a single dose formulation. The use of combinations can be employed to treat cancer in a patient. For example, the cancer can be a hematological malignancy. In some embodiments, the combinations can be used to increase the efficacy of the individual components, to overcome resistance to a particular agent, or to treat a refractory disease.

Provided herein is a method for treating a cancer in a patient, the method including administering to the patient a therapeutically effective amount of a PIM kinase inhibitor and combine with a compound that modifies and/or inhibits autophagy.

As used herein, the term "cancer" includes, but is not limited to, blood borne and solid tumors. Cancer refers to disease of blood, bone, organs, skin tissue, and the vascular system, including, but not limited to, cancers of the bladder, blood, bone, brain, breast, cervix, chest, colon, endometrium, esophagus, eye, head, kidney, liver, lung, lymph nodes, mouth, neck, ovaries, pancreas, prostate, rectum, renal, skin, stomach, testis, throat, and uterus. Specific cancers include, but are not limited to, leukemia (acute lymphocytic leukemia (ALL), acute lyelogenous leukemia (AML), chronic lymphocytic leukemia (CLL), chronic myelogenous leukemia (CML), hairy cell leukemia), mature B cell neoplasms (small lymphocytic lymphoma, B cell prolymphocytic leukemia, lymphoplasmacytic lymphoma (such as Waldenstrom's macroglobulinemia), splenic marginal zone lymphoma, plasma cell myeloma, plasmacytoma, monoclonal immunoglobulin deposition diseases, heavy chain diseases, extranodal marginal zone B cell lymphoma (MALT lymphoma), nodal marginal zone B cell lymphoma (NMZL), follicular lymphoma, mantle cell lymphoma, diffuse B cell lymphoma, diffuse large B cell lymphoma (DLBCL), mediastinal (thymic) large B cell lymphoma, intravascular large B cell lymphoma, primary effusion lymphoma and Burkitt lymphoma/leukemia), mature T cell and natural killer (NK) cell neoplasms (T cell prolymphocytic leukemia, T cell large granular lymphocytic leukemia, aggressive NK cell leukemia, adult T cell leukemia/lymphoma, extranodal NK/T cell lymphoma, enteropathy-type T cell lymphoma, hepatosplenic T cell lymphoma, blastic NK cell lymphoma, mycosis fungoides (Sezary syndrome), primary cutaneous anaplastic large cell lymphoma, lymphomatoid papulosis, angioimmunoblastic T cell lymphoma, unspecified peripheral T cell lymphoma and anaplastic large cell lymphoma), Hodgkin lymphoma (nodular sclerosis, mixed celluarity, lymphocyte-rich, lymphocyte depleted or not depleted, nodular lymphocyte-predominant), myeloma (multiple myeloma, indolent myeloma, smoldering myeloma), chronic myeloproliferative disease, myelodysplastic/myeloproliferative disease, myelodysplastic syndromes, immunodeficiency-associated lymphoproliferative disorders, histiocytic and dendritic cell neoplasms, mastocytosis, chondrosarcoma, Ewing sarcoma, fibrosarcoma, malignant giant cell tumor, myeloma bone disease, osteosarcoma, breast cancer (hormone dependent, hormone independent), gynecological cancers (cervical, endometrial, fallopian tube, gestational trophoblastic disease, ovarian, peritoneal, uterine, vaginal and vulvar), basal cell carcinoma (BCC), squamous cell carcinoma (SCC), malignant melanoma, dermatofibrosarcoma protuberans, Merkel cell carcinoma, Kaposi's sarcoma, astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, teratoma, malignant mesothelioma (peritoneal mesothelioma, pericardial mesothelioma, pleural mesothelioma), gastro-enteropancreatic or gastroenteropancreatic neuroendocrine tumor (GEP-NET), carcinoid, pancreatic endocrine tumor (PET), pancreatic adenocarcinoma, colorectal adenocarcinoma, colorectal carcinoma, aggressive neuroendocrine tumor, leiomyosarcomamucinous adenocarcinoma, Signet Ring cell adenocarcinoma, hepatocellular carcinoma, cholangiocarcinoma, hepatoblastoma, hemangioma, hepatic adenoma, focal nodular hyperplasia (nodular regenerative hyperplasia, hamartoma), non-small cell lung carcinoma (NSCLC) (squamous cell lung carcinoma, adenocarcinoma, large cell lung carcinoma), small cell lung carcinoma, lung cancer, thyroid carcinoma, prostate cancer (hormone refractory, androgen independent, androgen dependent, hormone-insensitive), and soft tissue sarcomas (fibrosarcoma, malignant fibrous hystiocytoma, dermatofibrosarcoma, liposarcoma, rhabdomyosarcoma leiomyosarcoma, hemangiosarcoma, synovial sarcoma, malignant peripheral nerve sheath tumor/neurofibrosarcoma, extraskeletal osteosarcoma).

Many tumors of the hematopoietic and lymphoid tissues are characterized by an increase in cell proliferation, or a particular type of cell. The chronic myeloproliferative diseases (CMPDs) are clonal hematopoietic stem cell disorders characterized by proliferation in the bone marrow of one or more of the myeloid lineages, resulting in increased numbers of granulocytes, red blood cells and/or platelets in the peripheral blood. CMPD can include chronic myelogenous leukemia, chronic neutrophilic leukemia, chronic eosinophilic leukemia, polycythaemia vera, chronic idiopathic myelofibrosis, essential thrombocythaemia and unclassifiable chronic myeloproliferative disease.

Provided herein is a method for treating a hematological malignancy in a patient, the method including administering to the patient a therapeutically effective amount of a PIM kinase inhibitor and in combination with a compound that modifies and/or inhibits the autophagy process.

The term "hematological malignancy" as used herein is meant to include cancers that affect one or more of the blood, bone marrow, and lymph nodes, such as acute lymphoblastic leukemia (ALL), acute myeloid leukemia (AML), chronic lymphocytic leukemia (CLL), chronic myelogenous leukemia (CML), hairy cell leukemia, AIDS-related lymphoma, B-cell lymphoma, cutaneous T-cell lymphoma, Hodgkin lymphoma, non-Hodgkin lymphoma, mycosis fungoides, primary central nervous system lymphoma, Sezary syndrome, Waldenstrom macroglobulinemia, chronic myeloproliferative disorders, Langerhans cell histiocytosis, multiple myeloma, plasma cell neoplasms, myelodysplastic syndromes, myelodysplastic neoplasms, and myeloproliferative neoplasms.

A "patient" as used herein refers to a mammal. For example, the mammal may be a mouse, rat, guinea pig, dog, monkey, or chimpanzee. Another example of a mammal is a human.

Administration

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories.

Although the dosage will vary depending on the symptoms, age and body weight of the patient, the nature and severity of the disorder to be treated or prevented, the route of administration and the form of the drug, in general, a daily dosage of from 0.001 to 200 mg of the different compounds is recommended for an adult human patient, and this may be administered in a single dose or in divided doses.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In solid dosage forms for oral administration (capsules, tablets, pills, powders, granules, and the like), the active ingredients are mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. Solid compositions of a similar type may also be employed as fillers in soft and hard-filled gelatin capsules using such excipients as lactose or milk sugars, as well as high molecular weight polyethylene glycols, and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the patient and adjusting the dosage and/or timing.

The concentration of a disclosed compounds in a pharmaceutically acceptable mixture will vary depending on several factors, including the dosage of the compound to be administered, the pharmacokinetic characteristics of the compound(s) employed, and the route of administration. In general, the compositions provided herein may be provided in an aqueous solution containing about 0.1-10% w/v of a compound disclosed herein, among other substances, for parenteral administration. Typical dose ranges are from about 0.01 to about 50 mg/kg of body weight per day, given in 1-4 divided doses. Each divided dose may contain the same or different compounds. The dosage will be an effective amount depending on several factors including the overall health of a patient, and the formulation and route of administration of the selected compound(s).

In some embodiments, the weight ratio of a PIM kinase inhibitor to a compound that inhibits autophagy providing for the synergistic effect on cancer cells lies within the range from about 1:800 to 1:1, more preferably from about 1:200 to 1:20. Concentrations of the PIM inhibitor can be in the range from about 0.001 μM to about 0.1 μM and the compound that inhibits autophagy can be in the range from about 0.001 μM to about 40 μM.

Examples

Reverse in-Gel Kinase Assay (RIKA)

The present invention shows that PIM kinase inhibitors disrupt and/or changes normal mRNA splicing, and can therefore be combined with others agents that modify and/or inhibit mRNA splicing. This was achieved by profiling PIM kinase substrates using a reverse in-gel kinase assay (RIKA) as described in U.S. Pat. No. 7,368,258, the contents included herein for all purposes, and determining that a suite of proteins that regulate mRNA splicing are direct targets of PIM kinase phosphotransferase activity. Briefly, the kinase is polymerized in a denaturing gel. The proteins are separated by two dimensional gel electrophoresis. The kinase and separated proteins are refolded in the gel using a de-escalating chaotropic agent gradient, for example, using decreasing molarities of urea. The kinase and separated proteins are incubated in isotopically labeled ATP, for example, $\gamma^{32}$P-ATP or $^{18}$O-ATP. This step labels the substrates for the kinase. Excess ATP is washed away by multiple washes and gels are visualized by autoradiography, or $^{18}$O-labeled peptides are extracted from the gel and identified using mass spectrometry.

The list of splicing-related direct PIM kinase targets is shown below in Table 1:

| Serial Number | Entry Name | Protein Name |
|---|---|---|
| 1 | SRSF1_HUMAN | Serine/arginine-rich splicing factor 1 OS = *Homo sapiens* GN = SRSF1 PE = 1 SV = 2 |
| 2 | SRSF5_HUMAN | Serine/arginine-rich splicing factor 5 OS = *Homo sapiens* GN = SRSF5 PE = 1 SV = 1 |
| 3 | SRSF6_HUMAN | Serine/arginine-rich splicing factor 6 OS = *Homo sapiens* GN = SRSF6 PE = 1 SV = 2 |
| 4 | SRSF7_HUMAN | Serine/arginine-rich splicing factor 7 OS = *Homo sapiens* GN = SRSF7 PE = 1 SV = 1 |
| 5 | SRS10_HUMAN | Serine/arginine-rich splicing factor 10 OS = *Homo sapiens* GN = SRSF10 PE = 1 SV = 1 |
| 6 | U2AF1_HUMAN | Splicing factor U2AF 35 kDa subunit OS = *Homo sapiens* GN = U2AF1 PE = 1 SV = 3 |
| 7 | CWC22_HUMAN | Pre-mRNA-splicing factor CWC22 *Homo*log OS = *Homo sapiens* GN = CWC22 PE = 1 SV = 3 |
| 8 | SF3B2_HUMAN | Splicing factor 3B subunit 2 OS = *Homo sapiens* GN = SF3B2 PE = 1 SV = 2 |
| 9 | SF01_HUMAN | Splicing factor 1 OS = *Homo sapiens* GN = SF1 PE = 1 SV = 4 |
| 10 | SFR19_HUMAN | Splicing factor, arginine/serine-rich 19 OS = *Homo sapiens* GN = SCAF1 PE = 1 SV = 3 |

-continued

| Serial Number | Entry Name | Protein Name |
|---|---|---|
| 11 | PR38A_HUMAN | Pre-mRNA-splicing factor 38A OS = Homo sapiens GN = PRPF38A PE = 1 SV = 1 |
| 12 | SPF45_HUMAN | Splicing factor 45 OS = Homo sapiens GN = RBM17 PE = 1 SV = 1 |
| 13 | SF3A2_HUMAN | Splicing factor 3A subunit 2 OS = Homo sapiens GN = SF3A2 PE = 1 SV = 2 |
| 14 | HNRL2_HUMAN | Heterogeneous nuclear ribonucleoprotein U-like protein 2 OS = Homo sapiens GN = HNRNPUL2 PE = 1 SV = 1 |
| 15 | HNRPC_HUMAN | Heterogeneous nuclear ribonucleoproteins C1/C2 OS = Homo sapiens GN = HNRNPC PE = 1 SV = 4 |
| 16 | ROA1_HUMAN | Heterogeneous nuclear ribonucleoprotein A1 OS = Homo sapiens GN = HNRNPA1 PE = 1 SV = 5 |
| 17 | ROA2_HUMAN | Heterogeneous nuclear ribonucleoproteins A2/B1 OS = Homo sapiens GN = HNRNPA2B1 PE = 1 SV = 2 |
| 18 | RA1L2_HUMAN | Heterogeneous nuclear ribonucleoprotein A1-like 2 OS = Homo sapiens GN = HNRNPA1L2 PE = 2 SV = 2 |
| 19 | ROA3_HUMAN | Heterogeneous nuclear ribonucleoprotein A3 OS = Homo sapiens GN = HNRNPA3 PE = 1 SV = 2 |
| 20 | HNRPM_HUMAN | Heterogeneous nuclear ribonucleoprotein M OS = Homo sapiens GN = HNRNPM PE = 1 SV = 3 |
| 21 | HNRDL_HUMAN | Heterogeneous nuclear ribonucleoprotein D-like OS = Homo sapiens GN = HNRNPDL PE = 1 SV = 3 |
| 22 | ROAA_HUMAN | Heterogeneous nuclear ribonucleoprotein A/B OS = Homo sapiens GN = HNRNPAB PE = 1 SV = 2 |
| 23 | ROAA_HUMAN | Heterogeneous nuclear ribonucleoprotein A/B OS = Homo sapiens GN = HNRNPAB PE = 1 SV = 2 |
| 24 | HNRPK_HUMAN | Heterogeneous nuclear ribonucleoprotein K OS = Homo sapiens GN = HNRNPK PE = 1 SV = 1 |
| 25 | HNRPL_HUMAN | Heterogeneous nuclear ribonucleoprotein L OS = Homo sapiens GN = HNRNPL PE = 1 SV = 2 |
| 26 | ROA3_HUMAN | Heterogeneous nuclear ribonucleoprotein A3 OS = Homo sapiens GN = HNRNPA3 PE = 1 SV = 2 |
| 27 | ROA0_HUMAN | Heterogeneous nuclear ribonucleoprotein A0 OS = Homo sapiens GN = HNRNPA0 PE = 1 SV = 1 |
| 28 | HNRPU_HUMAN | Heterogeneous nuclear ribonucleoprotein U OS = Homo sapiens GN = HNRNPUPE = 1 SV = 6 |

Combination of PIM Kinase Inhibitor (AZD1208) Synergizes with Autophagy Inhibitor Chloroquine in EOL1 Cells.

To demonstrate that PIM inhibition and autophagy inhibition synergize in human cancer cell growth inhibition, acute myeloid leukemia cells (EOL1) were treated at varying doses with a PIM kinase inhibitor alone (AZD 1208), an autophagy inhibitor alone (chloroquine) and in combination.

General experimental procedure: 20,000 (EOL1) cells were seeded per well in 96-well plates. After culturing overnight, AZD1208 and chloroquine were added to wells in quadruplicates at different concentrations. Different ratios between AZD1208 and chloroquine were tried in EOL1 cells. At 48 hours the MTT metabolism indicative of number of live cells was measured by MTT assay (Promega, Cat: G4000). The resulting values were used to evaluate the Fa (fraction affected) values, which were plugged into the CompuSyn software to calculate the combination indices (CI values) at ED50, ED75, ED90 and ED95 (ED—Effective dose of combination).

TABLE 1

| AZD1208 (µM) | Effect | chloroquine (µM) | Effect | Combination (µM) | Effect |
|---|---|---|---|---|---|
| 0.1 | 0.639 | 20 | 0.600 | 20.1 | 0.955 |
| 0.05 | 0.505 | 10 | 0.397 | 10.05 | 0.823 |
| 0.25 | 0.386 | 5 | 0.257 | 5.025 | 0.645 |

These values of drug dose and effect (FA values wherein FA is the fraction of cell death induced by drug treatment. It ranges from 0-1, with the Fa value of 0 meaning no cell killing and the value of 1 representing 100% of cell killing) is shown in Table 1. The data were analyzed using CompuSyn, an algorithm based on the Chao-Talalay method for detecting drug synergy (3). The results are shown in Table 3 below. Synergy, indicated by a combination index (CI) value<1 was observed at multiple drug doses. The following in Table 2 shows the level of synergy.

TABLE 2

| Synergism | | Antagonism | |
|---|---|---|---|
| CI value | Synergy category | CI value | Antagonism category |
| 0.85-0.9 | Slight synergy | 1.1-1.2 | Slight antagonism |
| 0.7-0.85 | Moderate synergy | 1.2-1.45 | Moderate antagonism |
| 0.3-0.7 | synergy | 1.45-3.3 | antagonism |
| 0.1-0.3 | Strong synergy | 3.3-10 | Strong antagonism |
| <0.1 | Very strong synergy | >10 | Very strong antagonism |

TABLE 3

| | GI | Experiment 1 | Experiment 2 | Experiment 3 | Average |
|---|---|---|---|---|---|
| CI value | 50% | 0.48996 | 0.52725 | 0.63132 | 0.54951 |
| | 75% | 0.35843 | 0.39585 | 0.43489 | 0.39639 |
| | 90% | 0.26259 | 0.29723 | 0.30292 | 0.28758 |
| | 95% | 0.21267 | 0.24461 | 0.23843 | 0.23190 |

Table 3. PIM kinase and autophagy inhibition synergize to inhibit leukemia cell growth. EOL1 acute myeloid leukemia cells were treated with AZD 1208 and chloroquine alone and in combination. CI values were determined using CompuSyn at 50%, 75%, 90%, and 95% growth inhibition (GI) Cell growth was measured using standard 3-(4,5-dimethylthiazol-2-yl)-2,5-diphenyltetrazolium bromide (MTT) assays. The results of three separate experiments are shown above in Table 3.

Combination of PIM Kinase Inhibitor (AZD1208) Synergizes with Autophagy Inhibitors (Chloroquine, Verteporfin or Bafilomycin A1) Testing was Also Conducted with Molm 16 Cells

TABLE 4

| AZD1208 (μM) | Effect | chloroquine (μM) | Effect | Combination (μM) | Effect (CI value) |
|---|---|---|---|---|---|
| 0.05 | 0.54968 | 40 | 0.46466 | 40.05 | 0.91680 (0.26039) |
| 0.025 | 0.35396 | 20 | 0.13761 | 20.025 | 0.52438 (0.41939) |
| 0.0125 | 0.24131 | 10 | 0.05357 | 10.0125 | 0.34034 (0.30854) |

The data presented in this Table 4 is from an experiment in which Molm16 cells were treated with AZD1208 in combination with choloroquine (AZD1208 μM:chloroquine μM=1:800). These are values of drug dose and effect (fraction of cells affected by the treatment—FA values). The treatment time is 72 hours.

TABLE 5

| AZD1208 (μM) | Effect | Verteporfin (μM) | Effect | Combination (μM) | Effect (CI value) |
|---|---|---|---|---|---|
| 0.1 | 0.64744 | 20 | 0.21427 | 20.1 | 0.74265 (0.22320) |
| 0.05 | 0.48468 | 10 | 0.08412 | 10.05 | 0.54265 (0.19481) |

The data presented in this Table 5 is from an experiment in which Molm16 cells were treated with AZD1208 in combination with verteporfin (AZD1208 μM:verteporfin μM=1:200). These are values of drug dose and effect (fraction of cells affected by the treatment—FA values). The treatment time is 72 hours.

TABLE 6

| AZD1208 (μM) | Effect | Bafilomycin A1 (μM) | Effect | Combination (μM) | Effect (CI values) |
|---|---|---|---|---|---|
| 0.025 | 0.36147 | 0.025 | 0.82789 | 0.05 | 0.89020 (0.80032) |
| 0.0125 | 0.22592 | 0.0125 | 0.79983 | 0.025 | 0.83263 (0.60525) |
| 0.00625 | 0.171631 | 0.00625 | 0.47443 | 0.0125 | 0.51816 (1.13127) |

The data presented in this Table 6 is from an experiment in which Molm16 cells were treated with AZD1208 in combination with Bafilomycin A1 (AZD1208 μM:bafilomycin A1 μM=1:1). These are values of drug dose and effect (fraction of cells affected by the treatment—FA values). The treatment time is 48 hours.

These data demonstrate that PIM inhibition combined with autophagy inhibition result in strong synergy to inhibit the growth of cancer cells. These data further suggest that combining PIM inhibition with autophagy inhibition can represent an innovative new approach for treating patients with acute myeloid leukemias and other cancers.

REFERENCES

The contents of the following references are incorporated by reference herein for all purposes.
1. Frankel, L. B., Lubas, M., and Lund, A. H. (2017) Emerging connections between RNA and autophagy. Autophagy 13, 3-23.
2. Levy, J. M. M., Towers, C. G., and Thorburn, A. (2017) Targeting autophagy in cancer. Nat Rev Cancer 17, 528-542.
3. Chou, T. C., and Talalay, P. (1984) Quantitative analysis of dose-effect relationships: the combined effects of multiple drugs or enzyme inhibitors. Adv Enzyme Regul 22, 27-55.

That which is claimed is:

1. A method of treating acute myeloid leukemia (AML), the method comprising administering to a subject in need of such treatment a composition comprising at least one PIM kinase modulator/inhibitor that exhibits changes in expression of RNA binding protein and/or ribosomal proteins in combination with a compound that inhibits autophagy, wherein the PIM kinase inhibitor is AZD1208 ((5E)-5-[[2-[(3R)-3-aminopiperidin-1-yl]-3-phenylphenyl]methylidene]-1,3-thiazolidine-2,4-dione) and compound that inhibits autophagy is selected from the group consisting of chloroquine, Bafilomycin Al, and Verteporfin.

2. The method of claim 1, wherein administration of the PIM kinase inhibitor and the compound that inhibits autophagy is administered concurrently or sequentially.

3. The method of claim 1, wherein the least one PIM kinase modulator/inhibitor that exhibits changes in expression of RNA binding protein and/or ribosomal proteins and the compound that inhibits autophagy has a molar ratio within the range from about 1:800 to 1:1.

4. The method of claim 1, wherein the least one PIM kinase modulator/inhibitor that exhibits changes in expression of RNA binding protein and/or ribosomal proteins and the compound that inhibits autophagy has a molar ratio of about 1:200.

5. A composition comprising a combination of therapeutically synergistic amounts of at least one a PIM kinase inhibitor that exhibits changes in expressed RNA or ribosomal binding proteins in combination with a compound that inhibits autophagy, wherein the PIM kinase inhibitor is AZD1208 ((5E)-5-[[2-[(3R)-3-aminopiperidin-1-yl]-3-phenylphenyl]methylidene]-1,3-thiazolidine-2,4-dione) and compound that inhibits autophagy is selected from the group consisting of chloroquine, Bafilomycin Al, and Verteporfin, wherein the combination has a therapeutic effect on acute myeloid leukemia (AML).

6. The composition of claim 5, wherein the therapeutically synergistic amounts of at least one a PIM kinase inhibitor that exhibits changes in expressed RNA or ribosomal binding proteins in combination with a compound that inhibits autophagy has a molar ratio within the range from about 1:800 to 1:1.

7. The composition of claim 5, wherein the therapeutically synergistic amounts of at least one a PIM kinase inhibitor that exhibits changes in expressed RNA or ribosomal binding proteins in combination with a compound that inhibits autophagy has a molar ratio of about 1:200.

* * * * *